United States Patent
Molinelli et al.

(10) Patent No.: US 9,579,557 B1
(45) Date of Patent: Feb. 28, 2017

(54) SWING TRAINING DEVICE AND METHOD OF USING SAME

(71) Applicants: James L. Molinelli, Bronx, NY (US); Albert M. Torressen, Bronx, NY (US)

(72) Inventors: James L. Molinelli, Bronx, NY (US); Albert M. Torressen, Bronx, NY (US)

(*) Notice: Subject to any disclaimer, the term of this patent is extended or adjusted under 35 U.S.C. 154(b) by 0 days.

(21) Appl. No.: 15/078,780

(22) Filed: Mar. 23, 2016

(51) Int. Cl.
*A63B 69/36* (2006.01)
*A63B 71/06* (2006.01)
*A63B 69/00* (2006.01)
*A63B 69/38* (2006.01)

(52) U.S. Cl.
CPC ......... *A63B 71/0622* (2013.01); *A63B 69/00* (2013.01); *A63B 69/0002* (2013.01); *A63B 69/0024* (2013.01); *A63B 69/36* (2013.01); *A63B 69/38* (2013.01); *A63B 2069/0008* (2013.01); *A63B 2071/0633* (2013.01); *A63B 2220/40* (2013.01)

(58) Field of Classification Search
USPC ....... 473/223, 224, 234, 409, 422, 437, 457, 473/451
See application file for complete search history.

(56) References Cited

U.S. PATENT DOCUMENTS

| | | | | |
|---|---|---|---|---|
| 3,498,616 A | * | 3/1970 | Hurst | A63B 69/3635 473/234 |
| 4,789,160 A | * | 12/1988 | Dollar, Jr. | A63B 69/3635 473/223 |
| 5,911,635 A | * | 6/1999 | Ogden | A63B 69/3632 473/224 |
| 6,923,737 B1 | | 8/2005 | Walker | |
| 8,137,219 B2 | | 3/2012 | Gant | |
| 8,398,502 B2 | * | 3/2013 | Iwahashi | A63B 69/3632 473/223 |
| 8,622,854 B2 | | 1/2014 | Suzuki | |
| 8,827,847 B2 | | 9/2014 | Johnson | |
| 8,888,614 B2 | | 11/2014 | Nutter | |
| 8,911,309 B1 | | 12/2014 | Harihar et al. | |

* cited by examiner

Primary Examiner — Nini Legesse
(74) Attorney, Agent, or Firm — James R McDaniel

(57) ABSTRACT

A one-piece swing training device, comprising: a tapered sporting implement attachment section having a narrower end portion located at one end of the sporting implement attachment section and a wider end portion located at another end of the sporting implement attachment section, wherein the sporting implement attachment section is removably attached to a section of a sporting implement; and a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained to the removable magnetized end cap.

18 Claims, 7 Drawing Sheets

SWING TRAINING DEVICE AND METHOD OF USING SAME

FIELD OF THE INVENTION

This invention relates generally to swing training devices and more particularly to a swing training device that is capable of being removably attached to the shaft of a sporting implement such that an audible sound and light are emitted by the swing training device in order to inform the user when the user has broken his/her wrist during the swing thereby improving the user's swing.

It is known that during a correct swing of a baseball bat, for example, the batter's legs, hips, torso and arms must first go in motion. Thereafter, the batter's arms and hands come across the batter's torso. Once the batter's arms and hands have come across the batter's torso, the batter should roll or "break" his/her wrists.

A common problem with a batter in baseball, for example, is that the batter is "breaking his wrists" too quickly before making contact with the baseball. This premature rolling of the wrists before or near contact with the baseball is a serious mechanical flaw that results in loss of swing power and swing consistency. This is because the premature rolling of the wrists causes the lead elbow of the batter to start breaking down-and-in too soon which alters the natural trajectory or plane of the batter's swing.

BACKGROUND OF THE INVENTION

Prior to the present invention, as set forth in general terms above and more specifically below, it is known, to employ various swing training devices. See for example, U.S. Pat. No. 6,923,737 by Walker, U.S. Pat. No. 8,137,219 by Gant, U.S. Pat. No. 8,622,854 by Suzuki, U.S. Pat. No. 8,827,847 by Johnson, U.S. Pat. No. 8,888,614 by Nutter, and U.S. Pat. No. 8,911,309 by Harihar et al. While these various swing training devices may have been generally satisfactory, there is nevertheless a need for a new and improved swing training device that is capable of being removably attached to the shaft of a sporting implement such that an audible sound and light are emitted by the swing training device in order to inform the user when the user has broken his/her wrists during the swing thereby improving the user's swing power and swing consistency.

It is a purpose of this invention to fulfill this and other needs in the art in a manner more apparent to the skilled artisan once given the following disclosure.

SUMMARY OF THE INVENTION

A first aspect of the present invention is a one-piece swing training device, comprising: a tapered sporting implement attachment section having a narrower end portion located at one end of the sporting implement attachment section and a wider end portion located at another end of the sporting implement attachment section, wherein the sporting implement attachment section is removably attached to a section of a sporting implement; and a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained to the removable magnetized end cap.

In one embodiment of the first aspect of the present invention, the sporting implement attachment section is constructed of a durable, clear, scratch resistant, haze resistant, high impact resistant, crack resistant, temperature resistant, wear resistant, UV stabilized polymeric material that is capable of flexing so as to be easily attached to the sporting implement.

In another embodiment of the first aspect of the present invention, the removable end cap is constructed of a durable, rigid, scratch resistant, haze resistant, high impact resistant, crack resistant, temperature resistant, wear resistant, UV stabilized material, wherein the material is selected based upon the type of sound that is needed in order to provide an audible feedback to the user.

In another embodiment of the first aspect of the present invention, the sporting implement attachment section is further comprised of: a slot opening located along a length of the sporting implement attachment section.

In yet another embodiment of the first aspect of the present invention, the sporting implement attachment section is further comprised of: a cylindrical shaped cross-section.

In still yet another embodiment of the first aspect of the present invention, the sporting implement attachment section is further comprised of: a square or rectangular shaped cross-section.

In yet another embodiment of the first aspect of the present invention, the sporting implement attachment section is further comprised of: an accelerometer system.

In another embodiment of the first aspect of the present invention, the cylindrical tube is constructed of a durable, scratch resistant, haze resistant, high impact resistant, crack resistant, temperature resistant, wear resistant, UV stabilized polymeric material.

In yet another embodiment of the first aspect of the present invention, the cylindrical tube is further comprised of: an accelerometer system.

In yet another embodiment of the first aspect of the present invention, the swing training device is further comprised of a magnetized, adjustable retaining rod removably attached to the removable magnetized end cap at one end of the magnetized retaining rod such that the adjustable weight is retained on the other end of the magnetized retaining rod.

In still yet another embodiment of the first aspect of the present invention, the adjustable weight is further comprised of: a durable, rigid, high impact resistant, crack resistant, temperature resistant, wear resistant, UV stabilized metallic material.

In yet another embodiment of the first aspect of the present invention, the adjustable weight is further comprised of: a spherical ball.

In a further embodiment of the first aspect of the present invention, the removable end cap is further comprised of: a LED operatively connected to the removable end cap.

A second aspect of the present invention is a one-piece swing training device for use on sporting implements having a substantially straight shaft, comprising: a tapered sporting implement attachment section having a narrower end portion located at one end of the sporting implement attachment section and a wider end portion located at another end of the sporting implement attachment section; a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained on the removable magnetized end cap; and an adjustable insert located within the sporting implement attachment section such that the adjustable insert interacts with a section of a sporting implement having a straight shaft to assist in retaining the swing training device on the sporting implement.

In one embodiment of the second aspect of the present invention, the adjustable insert is further comprised of: a sporting implement sleeve having sleeve end portions.

In another embodiment of the second aspect of the present invention, wherein the removable end cap is constructed of a durable, rigid, scratch resistant, haze resistant, high impact resistant, crack resistant, temperature resistant, wear resistant, UV stabilized material, wherein the material is selected based upon the type of sound that is needed in order to provide an audible feedback to the user.

In another embodiment of the second aspect of the present invention, the sporting implement attachment section is further comprised of: an accelerometer system.

In another embodiment of the second aspect of the present invention, wherein the swing training device is further comprised of a magnetized, adjustable retaining rod removably attached to the removable magnetized end cap such that the adjustable weight is retained on the removable magnetized end cap.

In a third aspect of the present invention is a method of using a swing training device, wherein the swing training device includes a tapered sporting implement attachment section and a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained to the magnetized end cap, comprising the steps of: selecting, by a user, a type of a sporting implement to be used by the user; selecting a size of a swing training device that is to be removably attached to the sporting implement; selecting a desired magnetic strength of a magnetized end cap; selecting a desired size of an adjustable weight; inserting the weight into a cylindrical tube; fastening the removable magnetized end cap to the cylindrical tube; attaching the weight to the magnetized end cap; and attaching the sporting implement attachment section to the sporting implement.

In an embodiment of the third aspect of the present invention, the method is further comprised of the steps of: positioning the user in an initial swing stance; swinging the sporting implement such that wrists of the user are rolled thereby causing the adjustable weight to become separated from the magnetized retaining rod; impacting a removable end cap with the adjustable weight thereby causing the removable end cap to emit a sound and a light which are determinative as to when the wrists of the user were rolled; and measuring a velocity at which the user is swinging the sporting implement.

The preferred swing training device, according to various embodiments of the present invention, offers the following advantages: ease of use; portability; lightness in weight; durability; ability to be used on a variety of sporting implements; ability to audibly inform the user when the user has broken his/her wrists; ability to inform the user of the user's sporting implement swing speed; and ability to improve the user's swing power and swing consistency. In fact, in many of the preferred embodiments, these factors of ease of use, portability, lightness in weight, durability, ability to be used on a variety of sporting implements, ability to audibly and visually inform the user when the user has broken his/her wrists, ability to inform the user of the user's sporting implement swing speed, and ability to improve the user's swing power and consistency are optimized to an extent that is considerably higher than heretofore achieved in prior, known swing training devices.

BRIEF DESCRIPTION OF DRAWINGS

The above mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF PREFERRED EMBODIMENTS

Figure 1:
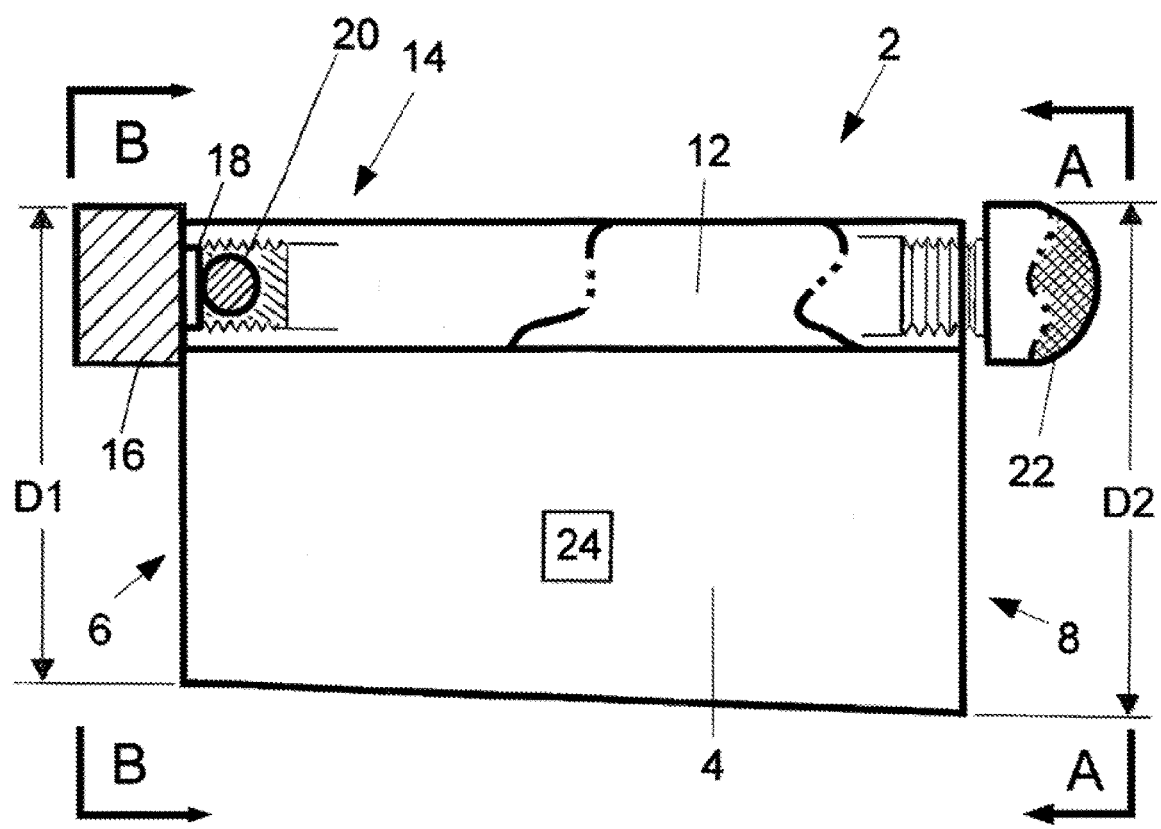
FIG. 1 is a partial cut away, side view of a swing training device, constructed according to the present invention.
Figure 3:
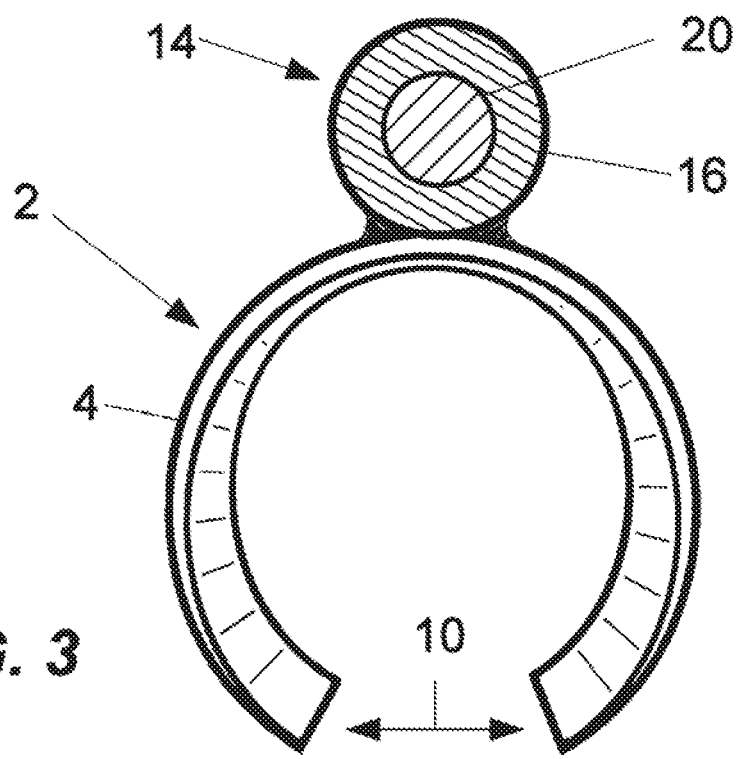
FIGS. 3 and 3A are end views of the swing training device, taken along the direction of arrows B-B in FIG. 1.

Referring now to the drawings and more particularly to FIGS. 1-6, there is illustrated a swing training device 2, which is constructed in accordance with the present invention. As will be explained hereinafter in greater detail, the swing training device 2 is constructed to be removably attached to a sporting implement such as a baseball/softball bat, golf club, tennis racket, hockey stick, squash racket, lacrosse stick, polo stick, hurling/shinty stick, ping pong paddle or the like, to provide an audible indication as to when the user has rolled or "broken" his/her wrists during the swinging of the sporting implement in order to improve the user's swing power and consistency. The advantages of swing training device 2 are ease of use of swing training device 2, the portability of swing training device 2, durability of swing training device 2, lightness in weight of swing training device 2, the ability of swing training device 2 to be used on a variety of sporting implements, the ability of swing training device 2 to audibly and visually inform the user when the user has broken his/her wrists, the ability of swing training device 2 to inform the user of the user's sporting implement swing speed, and the ability of swing training device 2 to improve the user's swing power and consistency.

Considering now the swing training device 2, in greater detail with reference to FIGS. 1-5, the swing training device 2 generally includes a sporting implement attachment section 4 and a cylindrical section 12. Preferably, swing training device 2 is constructed of a durable, clear, scratch resistant, haze resistant, high impact resistant, crack resistant, temperature resistant, wear resistant, UV stabilized polymeric material that is capable of flexing so as to be easily attached to the sporting implement. Preferably, swing training device 2 is constructed as a one-piece design however, it is to be understood that sporting implement attachment section 4 and a cylindrical section 12 can be constructed as two separate pieces and conventionally attached together through the use of adhesives, fusion bonding, welding, mechanical fasteners or the like. It is to be further understood that swing training device 2 should be located along a portion of the sporting implement so as to: not impede the ability of the sporting implement to contact the object that the sporting implement is intended to strike or hit; and not be contacted by the object that the sporting implement is intended to strike or hit. For example, the swing training device 2 should not be located on the baseball bat 104 (FIG. 8) where the swing training device 2 will interfere with the batter's ability to hit the baseball (FIG. 8) and the swing training device 2 should not be located on the baseball bat 104 so that the swing training device 2 will come into contact with the baseball 106.

Figure 8:
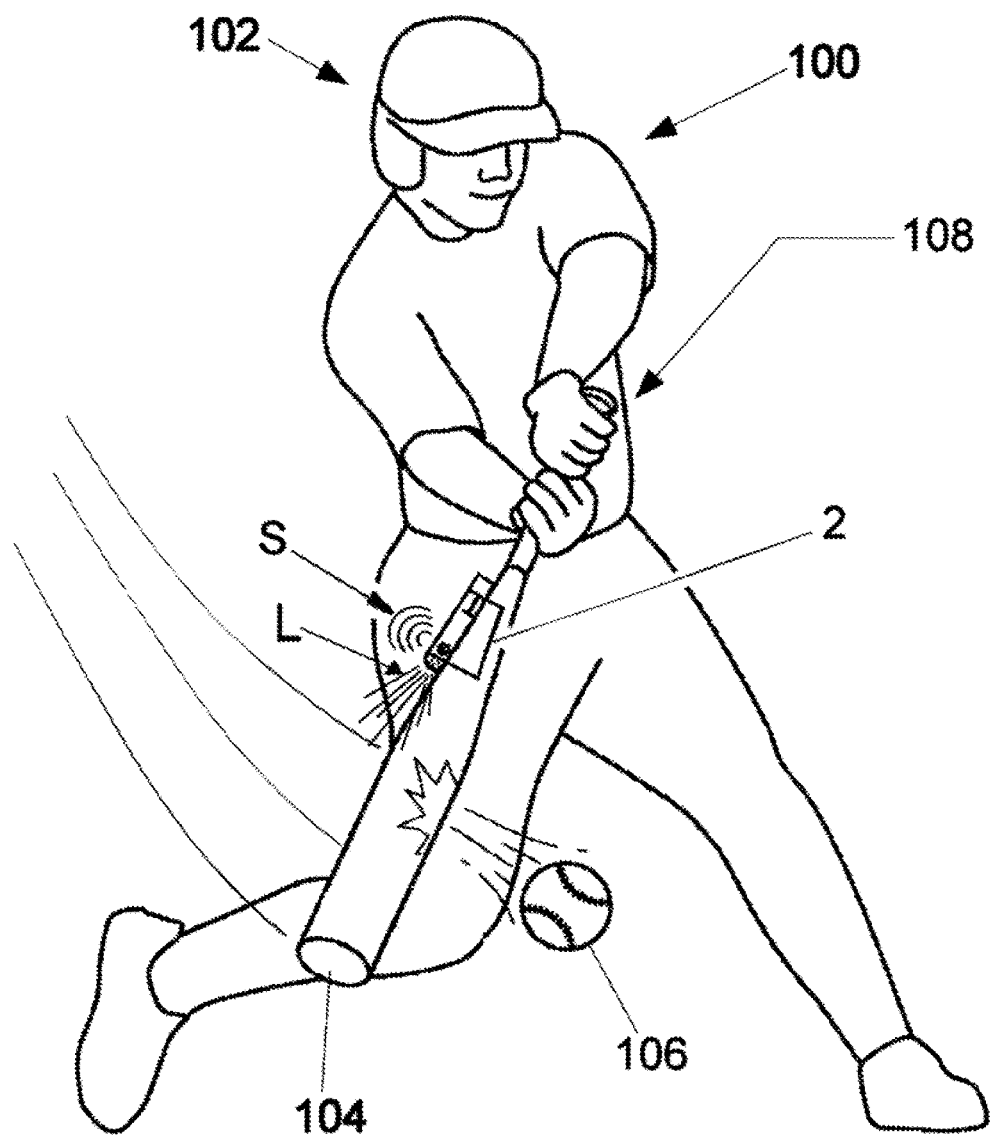
FIG. 8 is a schematic illustration of the swing training device being located on a baseball bat, wherein the batter is swinging the bat and the swing training device audibly notifies the batter when the batter has broken his/her wrists during the swing of the baseball bat.

Considering now sporting implement attachment section 4 in greater detail with respect to FIGS. 1-5, sporting implement attachment section 4 is tapered and includes narrower end portion 6 and wider end portion 8. Sporting implement attachment section 4 is used to attach swing training device 2 to a sporting implement such as a baseball bat 104 (FIG. 8). Sporting implement attachment section 4 is designed with narrower end portion 6 and wider end portion 8 so that as swing training device 2 slides along a length of the baseball bat 104, for example, wider end portion 8 engages a wider portion of the baseball bat 104 and narrower end portion 6 concurrently engages a narrower portion of the baseball bat 104 in order to firmly attach swing training device 2 to the baseball bat 104. Preferably, the length (L) of swing training device 2 ranges from 4-6 inches. Preferably, the diameter ($D_1$) of the narrower end portion 6 ranges from 1-1.5 inches. Preferably, the diameter ($D_2$) of the wider end portion 8 ranges from 1.5-2 inches. It is to be understood that while diameters $D_1$ and $D_2$ can vary, the important aspect is that the overall taper of swing training device 2 between narrower end portion 6 and wider end portion 8 must provide a continuous contact along the length of the swing training device 2, as swing training device 2 is attached to the sporting implement.

Located along the length of sporting implement attachment section 4 is slot opening 10. Slot opening 10, preferably, is constructed such that swing training device 2 can be easily slid over a portion of the sporting implement without adversely affecting the structural characteristics of swing training device 2 or the sporting implement. For example, slot opening 10 should be wide enough so as to be able to easily slide over the shaft of baseball bat 104 at a narrower portion of baseball bat 104. In this manner, once the swing training device 2 has been placed over baseball bat 104, swing training device 2 is then positioned along the length of the baseball bat 104 until swing training device 2 is firmly attached to baseball bat 104.

Figure 2:
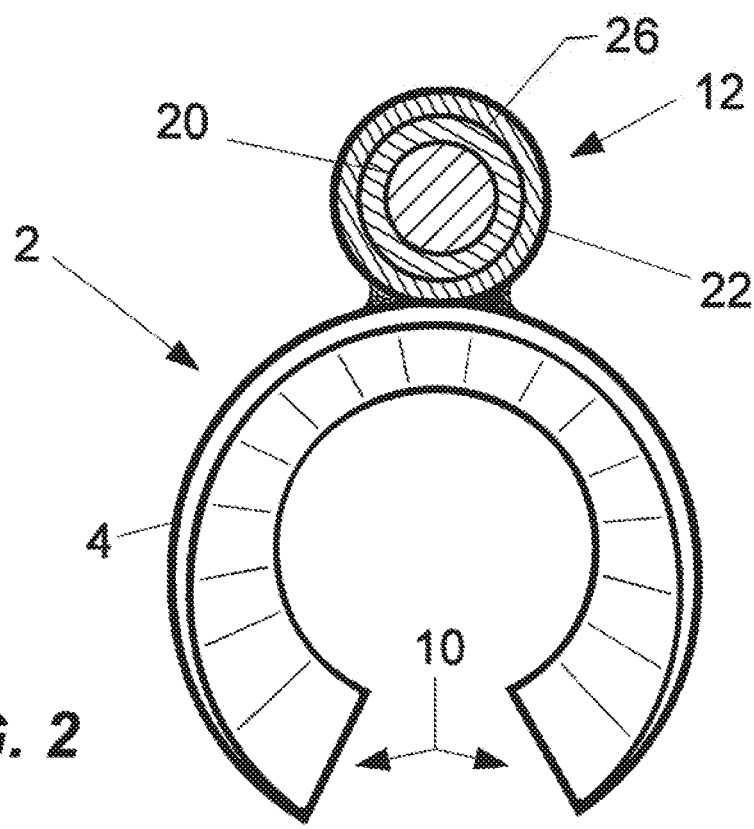
FIGS. 2 and 2A are end views of the swing training device, taken along the direction of arrows A-A in FIG. 1.
Figure 2A:
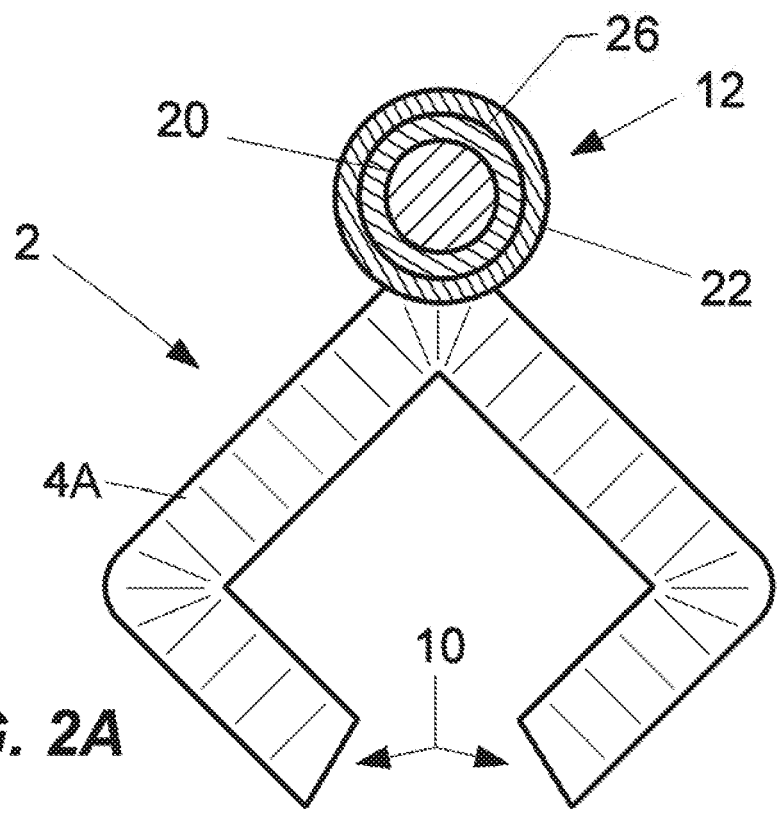
Figure 3A:
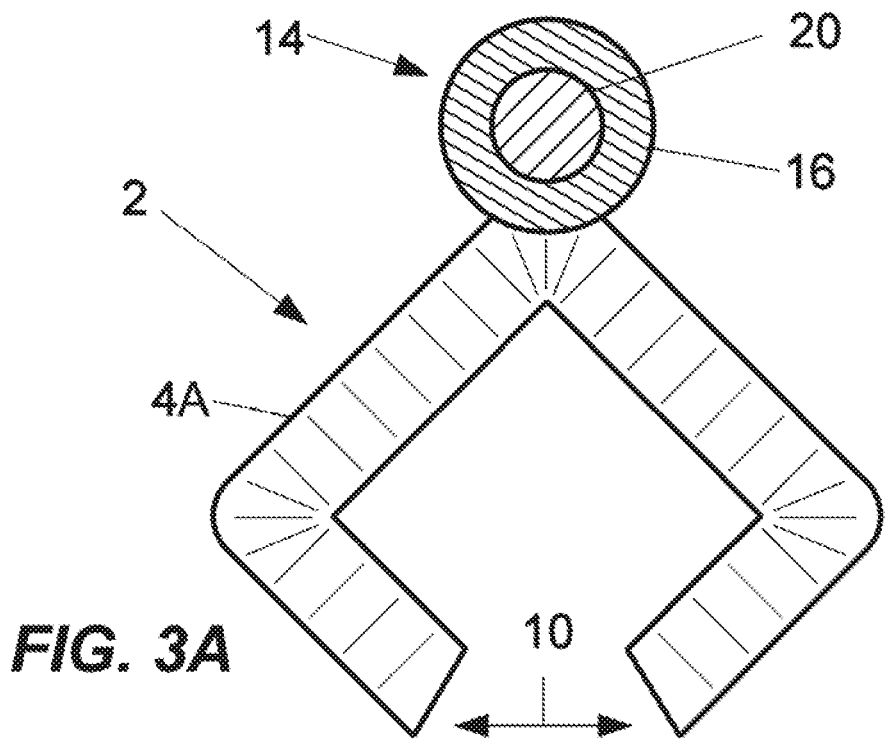
Figure 4:
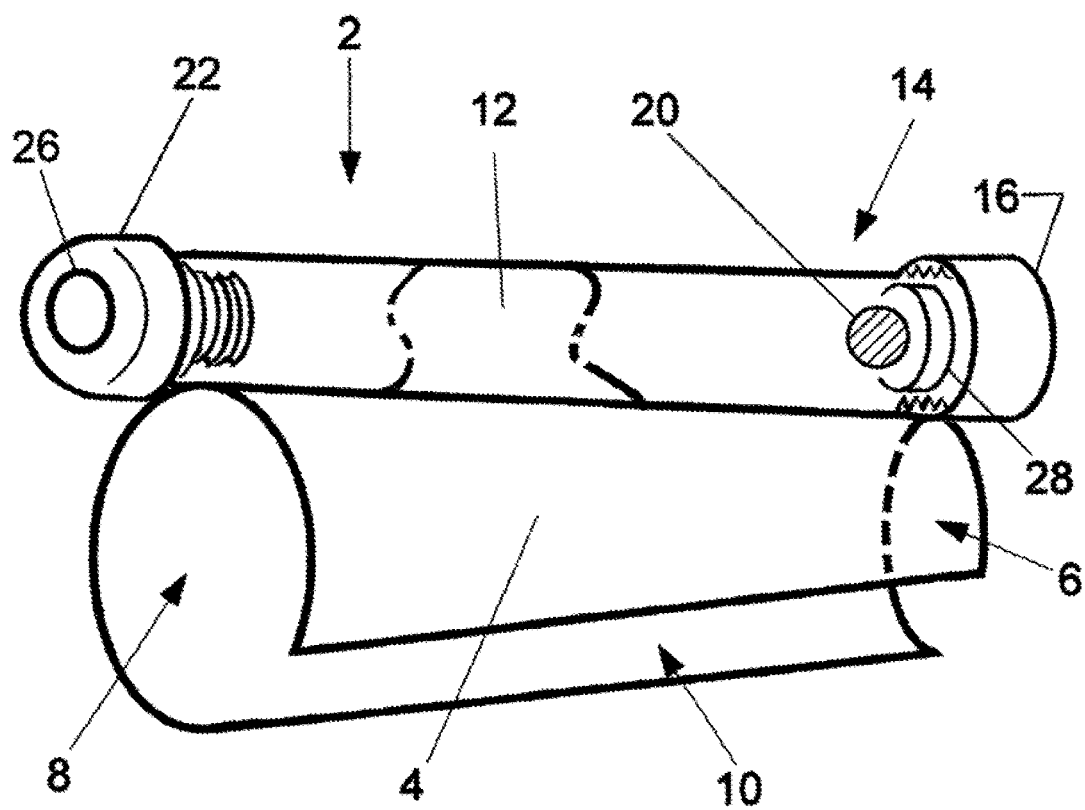
FIG. 4 is a partial cut away, perspective view of the swing training device, constructed according to the present invention.
Figure 5:
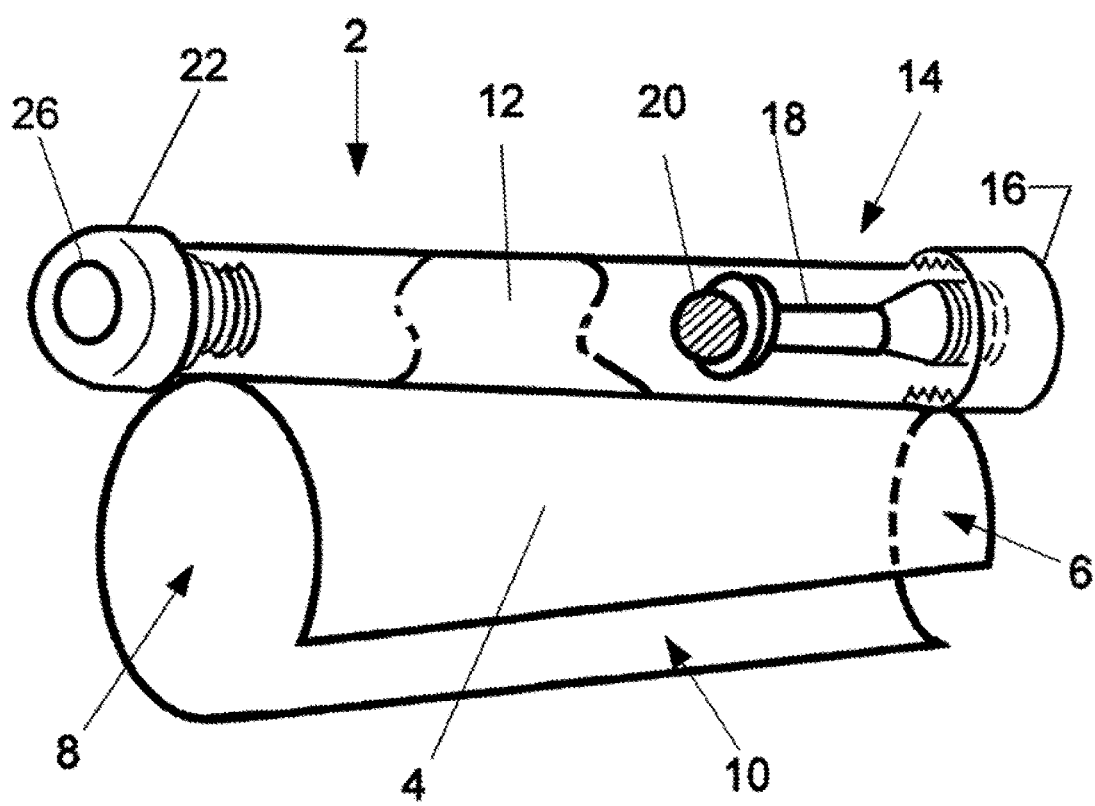
FIG. 5 is another partial cut away, perspective view of the swing training device, constructed according to the present invention.

It is to be understood that with respect to sporting implement attachment section 4, sporting implement attachment section 4, preferably, has a cylindrical shape as shown in FIGS. 4 and 5 in order to accommodate the cylindrical shape of the baseball bat 104. However, it is to be further understood that sporting implement attachment section 4 can be constructed of a variety of shapes depending upon the sporting implement to which the swing training device 2 is attached. For example, if the sporting implement is a hockey stick, it is known that hockey sticks generally have a square or rectangular cross-section. Consequently, sporting implement attachment section 4A could then be constructed with a square or rectangular shape in order to properly fit over the hockey stick, as shown in FIGS. 2A and 3A.

Considering now cylindrical section 12 in greater detail with respect to FIGS. 1-5, cylindrical section 12 includes weight retaining system 14, cylindrical tube 15, magnetized removable end cap 22, and light emitting diode (LED) 26. Weight retaining system 14 includes magnetized removable end cap 16, optional magnetized retaining rod 18 (as best seen in FIG. 5), and weight 20. Removable magnetized end cap 16, preferably, is constructed of a suitable durable, rigid, scratch resistant, haze resistant, high impact resistant, crack resistant, temperature resistant, wear resistant, UV stabilized material that is capable of being magnetized. It is to be understood that magnetized end cap 16 is constructed so that it can threadably engage tube 15 at threaded connection 17 so that magnetized end cap 16 can be removed from tube 15/attached to tube 15 by unscrewing/screwing magnetized end cap 16 out of/into tube 15 at threaded connection 17. The purpose of the removable aspect of end cap 16 will be discussed in greater detail below.

With respect to magnetized end cap 16, it is to be understood that a magnetic plate 28 or other similar magnetic device can be conventionally attached to the threaded end of end cap 16 in order to provide the desired amount of magnetic force which causes weight 20 to be held in place by end cap 16, as best seen in FIG. 4. It is also to be further understood that magnetic plate 28 may be omitted and end cap 16 itself may be conventionally magnetized. However, as will be discussed in greater detail later, an important feature of the present invention is that the magnetic attraction between magnetized end cap 16 and weight 20 must be just enough to retain weight 20 against magnetized end cap 16 until the user rolls or "breaks" his/her wrists during the swinging of the sporting implement.

With respect to optional magnetized retaining rod 18, magnetized retaining rod 18 is optional in that the user may decide to also use a magnetized retaining rod 18 that is magnetically attached to end cap 16, as best seen in FIG. 5. Magnetized retaining rod 18, preferably, is constructed of a suitable durable, rigid, high impact resistant, crack resistant, temperature resistant, wear resistant, UV stabilized metallic material. Magnetized retaining rod 18, preferably, ranges from 1-1.5 inches in length and 0.25-0.5 inches in diameter. Magnetized retaining rod 18 can be conventionally attached to end cap 16 by the use of magnets, adhesives, fusion bonding, welding, mechanical fasteners or the like. Magnetized retaining rod 18 can be used to retain the weight 20 through a desired amount of magnetic force which causes weight 20 to be held in place by magnetized retaining rod 18. However, as will be discussed in greater detail later, the magnetic attraction between magnetized retaining rod 18 and weight 20 must be just enough to retain weight 20 against magnetized retaining rod 18 until the user rolls or "breaks" his/her wrists during the swinging of the sporting implement.

It is to be understood that if the user desires to use a different end cap 16 that has a greater or lesser magnetic force, the user simply unscrews end cap 16 from threaded connection 17, selects another desired magnetized end cap 16, inserts the new magnetized end cap 16 into tube 15 and screws end cap 16 back into threaded connection 17.

Optionally, it is to be understood that if the user also desires to use a different magnetized retaining rod 18 that has a greater or lesser magnetic force, the user simply unscrews end cap 16 from threaded connection 17, selects the desired magnetized retaining rod 18 that may also be attached to end cap 16, attaches the new magnetized retaining rod 18 onto the end cap 16, inserts the new magnetized retaining rod 18 into tube 15 and screws end cap 16 back into threaded connection 17. For example, a Little League® baseball player may not need the amount of magnetic force in magnetized end cap 16 or, optionally, retaining rod 18 to retain weight 20 that a major league baseball player needs in order to cause weight 20 to be separated from magnetized end cap 16 or, optionally, magnetized retaining rod 18. If a younger player uses a magnetized end cap 16 or, optionally, magnetized retaining rod 18 that has a strong magnetic force, the younger player may have to swing the bat extremely fast in order to cause weight 20 to audibly and visually strike end cap 22. This excessive swinging action may adversely the younger player's swing power and consistency, thereby causing the younger player to develop an improper swing. Consequently, the younger player could employ a magnetized end cap 16 or, optionally, magnetized retaining rod 18 that is better suited for the younger player in that the magnetized end cap 16 or, optionally, magnetized retaining rod 18 may be weaker in terms of magnetic force. In this manner, the younger player can utilize swing training device 2 to more adequately assist the younger player in developing the proper batting swing power and consistency.

With respect to weight 20, weight 20, preferably, is a spherical shaped ball so that weight 20 can easily roll along tube 15. Weight 20, preferably, is constructed of a suitable durable, rigid, high impact resistant, crack resistant, temperature resistant, wear resistant, UV stabilized metallic material. Weight 20, preferably, has a diameter range of 0.25-0.5 inches. However, it is to be understood that the size of weight 20 can also be adjusted depending upon the strength and athletic ability of the user. As discussed above, a Little League® baseball player may need a smaller weight 20 than a major league baseball player needs. If a younger player uses a weight 20 that is too light, the younger player may have to swing the bat extremely fast in order to cause weight 20 to audibly and visually strike end cap 22. This excessive swinging action may adversely the younger player's swing power and consistency, thereby causing the younger player to develop an improper swing. Consequently, the younger player could employ a weight 20 that is better suited for the younger player. In this manner, the younger player can utilize swing training device 2 to more adequately assist the younger player in developing proper batting swing power and consistency.

With respect to tube 15, as discussed above, tube 15, preferably, is constructed of a durable, clear, scratch resistant, haze resistant, high impact resistant, crack resistant, temperature resistant, wear resistant, UV stabilized polymeric material. The inner diameter of tube 15, preferably, ranges from 0.5-0.75 inches.

With respect to removable end cap 22, removable end cap 22 includes a light emitting diode (LED) 26 or other suitable light emitting device that is conventionally attached to end cap 22, wherein the use of the LED 26 will be described in greater detail later. End cap 22, preferably, is constructed of a suitable durable, rigid, scratch resistant, haze resistant, high impact resistant, crack resistant, temperature resistant, wear resistant, UV stabilized material. It is to be understood that end cap 22 is constructed so that it can threadably engage tube 15 at threaded connection 23 so that end cap 22 can be removed from tube 15/attached to tube 15 by unscrewing/screwing end cap 22 out of/into tube 15 at threaded connection 23. It is to be understood that end cap 22 can be constructed of a variety of materials depending upon the type of sound that is needed in order to provide an audible and visual feedback to the user regarding the rolling or "breaking" of the user's wrists. The purpose of the removable aspect of end cap 22 will be discussed in greater detail later.

With respect to accelerometer system 24, accelerometer system 24 is conventionally attached to sporting implement attachment section 4. However, it is to be understood that accelerometer system 24 can also be conventionally attached to cylindrical section 12. As will be discussed in greater detail later, accelerometer 24 is an electromechanical device that can be used to conventionally measure, among other things, the dynamic acceleration or "g-force" and velocity at which the user is swinging or otherwise moving the sporting implement. After the dynamic acceleration and velocity has been measured, accelerometer system 24 conventionally transmits the dynamic acceleration and velocity measurements to the user. In this manner, the user is able to obtain real-time data about the user's bat swing velocity (otherwise known as "bat speed"), bat angle at the initial batting stance, and bat angle during the batting swing, for example.

With respect to LED 26, as discussed above, LED 26 is conventionally attached to end cap 22. As will be discussed in greater detail later, LED 26 is an electromechanical illumination device that can be used to conventionally notify the user that the user has rolled or "broken" his/her wrists. In particular, as will be described in greater detail later, once the user has rolled or "broken" his/her wrists, the weight 20 becomes dislodged from magnetic end cap 16 or, optionally, magnetic retaining rod 18 and strikes end cap 22. The force of the weight 20 striking end cap 22 will cause LED to conventionally illuminate or emit light. This lighting of LED 26 will then provide a visual feedback to the user that the user has rolled or "broken" his/her wrists.

Figure 6:
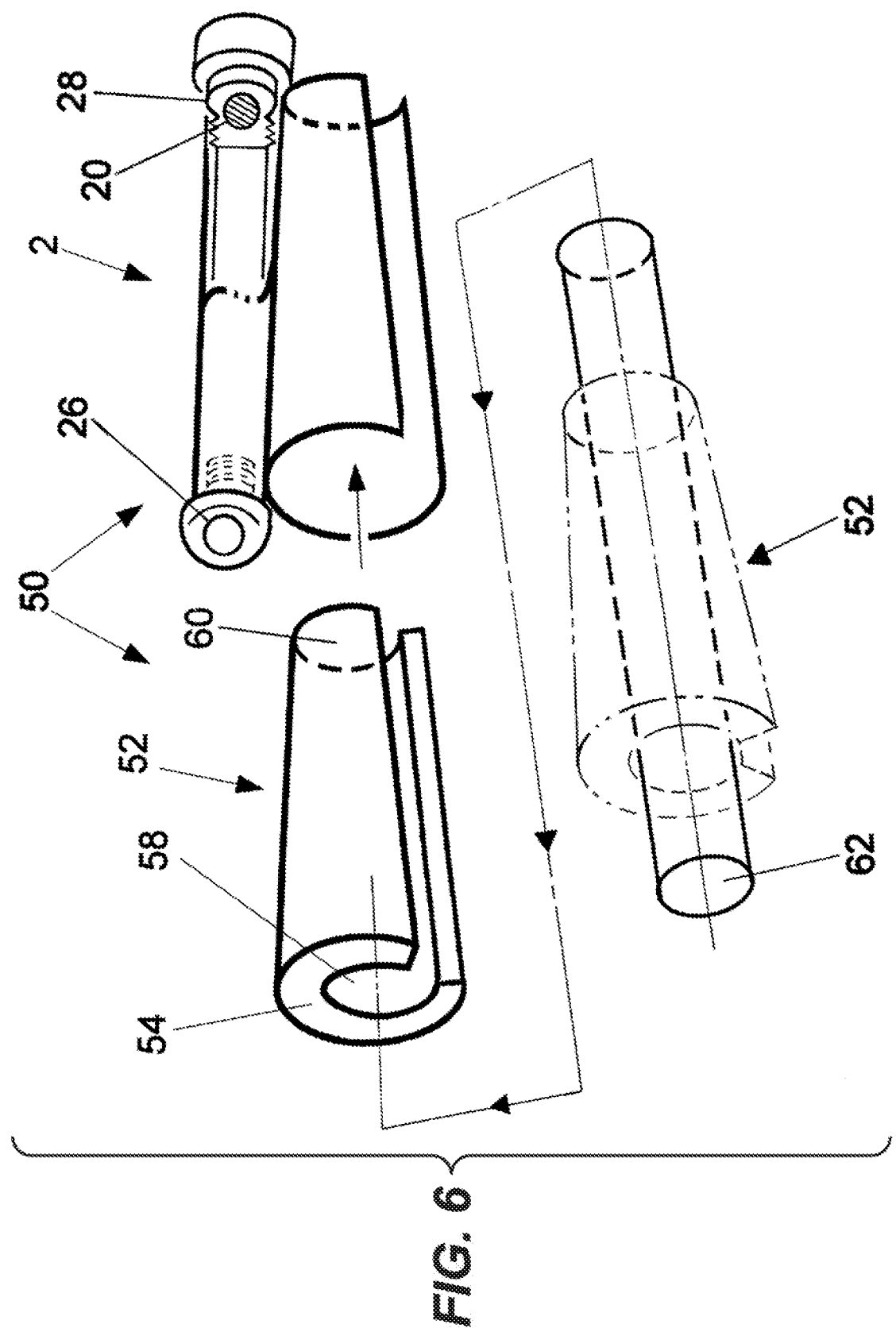
FIG. 6 is a perspective view of an adapter for using the swing training device on another type of sporting implement, constructed according to the present invention.

Considering now another swing training device 50, in greater detail with reference to FIG. 6, the swing training device 50 generally includes swing training device 2, adjustable insert 52, and a sporting implement shaft section 62. It is to be understood that swing training device 2 is constructed in the same manner, as described above.

Considering now adjustable insert 52, in greater detail with reference to FIG. 6, adjustable insert 52 includes sporting implement sleeve 54 and sleeve end portions 58 and 60. Sporting implement sleeve 54, preferably, is constructed of a suitable durable, lightweight, pliable, high impact resistant, crack resistant, temperature resistant, wear resistant, UV stabilized polymeric material that is capable of flexing so as to be easily attached to the sporting implement shaft section 62 and insertable within sporting implement attachment section 4. Preferably, the length of adjustable insert 52 is substantially the same as the length (L) of swing training device 2. Preferably, the inner diameter of the sleeve end portions 58 and 60 ranges from 0.25 to 2 inches. It is to be understood that while diameter of the sleeve end portions 58 and 60 can vary, the important aspect is that the sporting implement sleeve 54 must provide a continuous contact along the length of the swing training device 50 and sporting implement shaft section 62, as swing training device 50 is attached to the sporting implement shaft section 62. It is to be further understood that an outer diameter of sleeve end portion 58 will be greater than an outer diameter of sleeve end portion 60 so that adjustable insert 52 will remain within the tapered construction of sporting implement attachment section 4.

It is to be understood that swing training device 50 is to be used on a sporting implement which is substantially straight along the length of its shaft such as a golf club or a hockey stick, as opposed to a baseball bat which is substantially tapered along the length of the bat. In this manner, the user merely selects the type of sporting implement that is to be used. The user then selects the size of swing training device 50, assuming that the sporting implement has a substantially straight shaft length. The user subsequently fits the sporting implement sleeve 54 over the sporting implement shaft section 62 where the user desires to use the swing training device 50 and proceeds to use the swing training device, as will be discussed in greater detail later.

Figure 7:
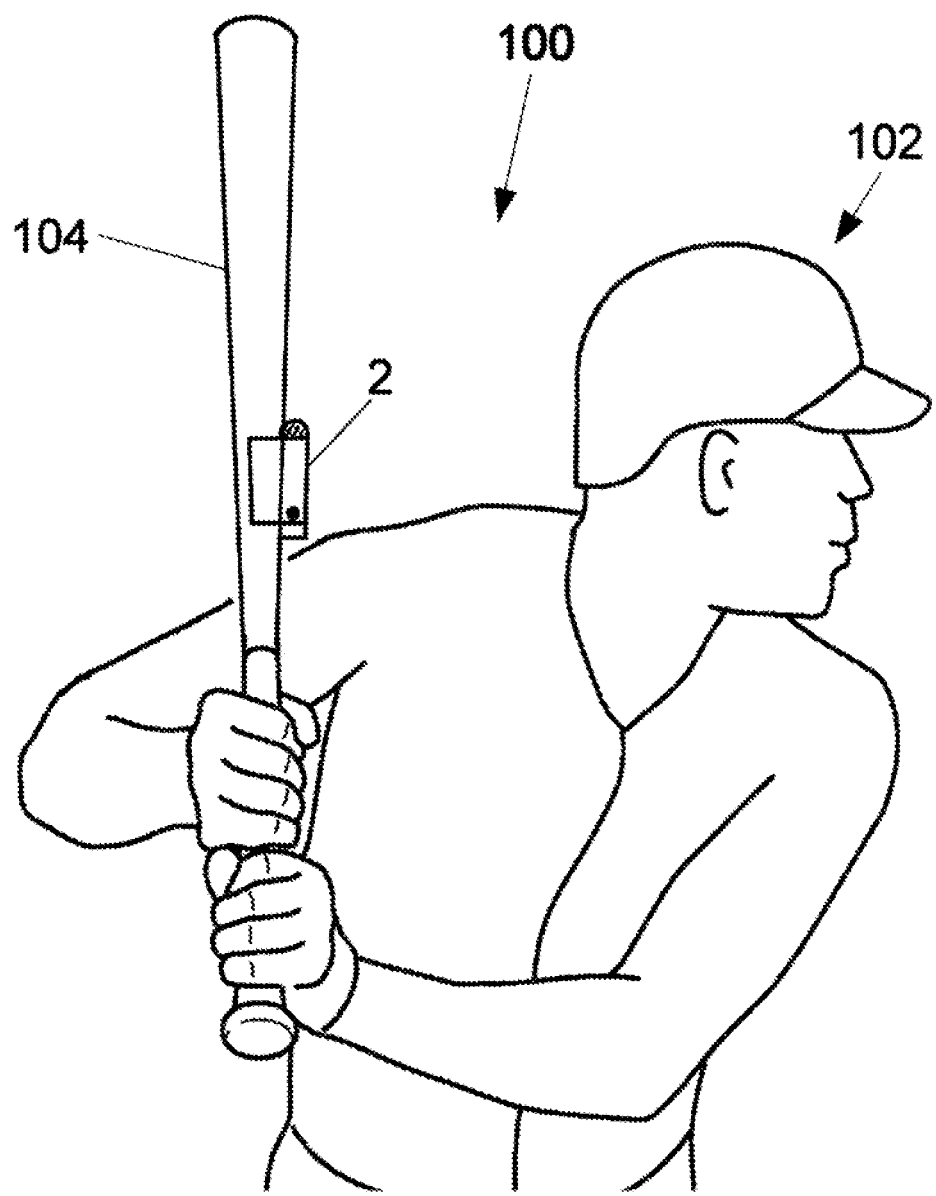
FIG. 7 is a schematic illustration of the swing training device being located on a baseball bat wherein the batter is preparing to swing the bat.

Considering now the method 100 of using swing training devices 2, 50 in greater detail with reference to FIGS. 7 and 8, the user (for example, a baseball batter 102) merely selects the type of sporting implement (for example, a baseball 104) that is to be used. It is to be understood that, as described above, swing training device 50 can be used on sporting implements which are substantially straight along the length of their shafts such as a golf club, a hockey stick, a tennis racket, a lacrosse stick, a squash racket, a polo stick, a hurling/shinty stick, a ping pong paddle or the like.

Once the user has selected the type of sporting implement to be used, the user then selects the size of swing training device 2, 50 that is to be removably attached to the sporting implement. As discussed above, it is also to be understood that the sporting implement may have a non-circular cross-section such as a hockey stick. Therefore, the user then has to select the desired cross-section of swing training device 2, 50. It is further to be understood that size of swing training device 2, 50 can also depend upon the size/l age of the user, the athletic ability of the user, the strength of the user and the like. For example, if the user is a major league baseball player, the user may opt to employ a longer swing training device 2, 50 so that the user is able to get more reliable results from swing training device 2, 50.

After the user has selected the size of swing training device 2, 50, the user then selects the desired magnetic strength of magnetized end cap 16 and/or optionally, magnetized retaining rod 18. As discussed above, a Little League® baseball player may not need the amount of magnetic force in magnetized end cap 16 and/or optionally, magnetized retaining rod 18 to retain weight 20 that a major league baseball player needs in order to cause weight 20 to be separated from magnetized end cap 16 and/or optionally, magnetized retaining rod 18. If a younger player uses a magnetized end cap 16 and/or optionally, magnetized retaining rod 18 that has a strong magnetic force, the younger player may have to swing the bat extremely fast in order to cause weight 20 to audibly strike end cap 22. This excessive swinging action may adversely the younger player's swing power and consistency, thereby causing the younger player to develop an improper swing. Consequently, the younger player could employ a magnetized end cap 16 and/or optionally, magnetized retaining rod 18 that is better suited for the younger player in that the magnetized end cap 16 and/or optionally, magnetized retaining rod 18 may be weaker in terms of magnetic force. In this manner, the younger player can utilize swing training device 2 to more adequately assist the younger player in developing proper batting swing power and consistency.

Once the user has selected the desired magnetic strength of magnetized end cap 16 and/or optionally, magnetized retaining rod 18, the user then selects the desired size of weight 20. As discussed above, a Little League® baseball player may need a smaller weight 20 than a major league baseball player needs. If a younger player uses a weight 20 that is too light, the younger player may have to swing the bat extremely fast in order to cause weight 20 to audibly strike end cap 22. This excessive swinging action may adversely the younger player's swing power and consistency, thereby causing the younger player to develop an improper swing. Consequently, the younger player could employ a weight 20 that is better suited for the younger player. In this manner, the younger player can utilize swing training device 2 to more adequately assist the younger player in developing proper batting swing power and consistency.

After the user has selected the desired magnetic strength of magnetized end cap 16 and the desired size of weight 20, the user inserts the weight 20 into tube 15 and fastens end cap 16 to tube 15, as discussed above. Optionally, if the user desires to use the magnetized retaining rod 18, the user attaches the magnetized retaining rod 18 to the end cap 16, inserts the weight 20 into tube 15, and fastens end cap 16/magnetized retaining rod 18 to tube 15, as similarly discussed above.

Once the desired weight retaining system 14 has been installed in swing training device 2, 50, the user then selects the desired end cap 22. For example, if swing training device 2, 50 is to be used in a batting cage where there is excessive noise, the user may want to employ an end cap 22 that emits a loud sound when it is impacted by weight 20. Conversely, if the user is using swing training device 2, 50 in a quieter setting, such as swinging a golf club at a driving range, the user may want to employ an end cap 22 that emits a quieter sound when it is impacted by weight 20. Once the user has selected the desired end cap 22, the user fastens end cap 22 to tube 15, as discussed above.

Now that the desired modifications have been made to swing training device 2, 50, the user selects the location on the sporting implement where swing training device 2, 50 is to be located. It is to be understood that the user should place swing training device 2, 50 in such a location on the sporting implement so that the object that is to be contacted by the sporting implement (such as a baseball 106) does not come into contact with swing training device 2, 50.

Consider now an example of how swing training device 2, 50 can be used to determine when a user roll or "breaks" his/her wrists with reference to FIGS. 7 and 8. In this example, a baseball player 102 is illustrated. As shown in FIGS. 7 and 8, the baseball player 102 has selected the desired modifications to swing training device 2 and located swing training device 2 along a section of the baseball bat 104 where, ideally, swing training device 2 will not come into contact with baseball 106.

As shown more dearly in FIG. 7, the baseball player 102 has positioned himself/herself in a conventional batting swing stance. In this position, weight 20 is located against and retained by magnetized end cap retaining rod 18.

Considering now FIG. 8, the baseball 106 has been thrown in the direction of the baseball player 102 and the baseball player 102 has begun to swing the baseball bat 104. As discussed above, ideally, the legs, hips, torso and arms of the baseball player 102 must first go in motion. Thereafter, the arms and hands of the baseball player 102 come across the torso of the baseball player 102. Once the arms and hands of the baseball player 102 have come across the torso of the baseball player 102, the baseball player 102 should roll or "break" his/her wrists 108.

Once the baseball player 102 has rolled or "broken" his/her wrists, the force of this action causes weight 20 to become separated from magnetized end cap 16 (FIG. 4) or magnetized retaining rod 18 (FIG. 5). The separation of weight 20 from magnetized end cap 16 or magnetized retaining rod 18 and the force of the swinging action by the baseball player 102 causes weight 20 to roll or otherwise traverse the length of tube 15 and impact end plate 22. The impact of weight 20 against end cap 22 (FIG. 4) causes a sound (S) for end cap 22 and a light (L) from the LED 26 (FIG. 4) to be emitted from swing training device 2. In this manner, the baseball player 102 can determine both audibly and visually if he/she performed the batting swing improperly by rolling or "breaking" his/her wrists 108 too early.

As discussed above, in addition to the audible feedback that the user can obtain when the weight 20 impacts end cap 22 upon the rolling or "breaking" of the user's wrists, the user can also obtain information from accelerometer system 24. In this manner, the user is able to obtain real-time data about the user's bat swing velocity (otherwise known as "bat speed"), bat angle at the initial batting stance, and bat angle during the batting swing and the like.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

Applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein is a new and improved swing training device and a novel method of using the swing training device. The preferred swing training device, according to various embodiments of the present invention, offers the following advantages: ease of use; portability; lightness in weight; durability; ability to be used on a variety of sporting implements; ability to audibly inform the user when the user has broken his/her wrists; ability to inform the user of the user's sporting implement swing speed; and ability to improve the user's swing power and consistency. In fact, in many of the preferred embodiments, these factors of ease of use, portability, lightness in weight, durability, ability to be used on a variety of sporting implements, ability to audibly and visually inform the user when the user has broken his/her wrists, ability to inform the user of the user's sporting implement swing speed, and ability to improve the user's swing power and consistency are optimized to an extent that is considerably higher than heretofore achieved in prior, known swing training devices.

We claim:

1. A one-piece swing training device, comprising:
a tapered sporting implement attachment section having a narrower end portion located at one end of the sporting implement attachment section and a wider end portion located at another end of the sporting implement attachment section, wherein the sporting implement attachment section is removably attached to a section of a sporting implement; and
a cylindrical section operatively attached to the sporting implement attachment section, wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained on the magnetized end cap and wherein the removable end cap includes a LED operatively connected to the removable end cap.

2. The swing training device, as in claim 1, wherein the sporting implement attachment section is constructed of a durable, clear, scratch resistant, haze resistant, high impact resistant, crack resistant, temperature resistant, wear resistant, UV stabilized polymeric material that is capable of flexing so as to be easily attached to the sporting implement.

3. The swing training device, as in claim 1, wherein the removable end cap is constructed of a durable, rigid, scratch resistant, haze resistant, high impact resistant, crack resistant, temperature resistant, wear resistant, UV stabilized material, wherein the material is selected based upon the type of sound that is needed in order to provide an audible feedback to the user.

4. The swing training device, as in claim 1, wherein the sporting implement attachment section is further comprised of:
a slot opening located along a length of the sporting implement attachment section.

5. The swing training device, as in claim 1, wherein the sporting implement attachment section is further comprised of:
a cylindrical shaped cross-section.

6. The swing training device, as in claim 1, wherein the sporting implement attachment section is further comprised of:
a square or rectangular shaped cross-section.

7. The swing training device, as in claim 1, wherein the sporting implement attachment section is further comprised of:
an accelerometer system.

8. The swing training device, as in claim 1, wherein the cylindrical tube is constructed of a durable, scratch resistant, haze resistant, high impact resistant, crack resistant, temperature resistant, wear resistant, UV stabilized polymeric material.

9. The swing training device, as in claim 1, wherein the cylindrical tube is further comprised of:
an accelerometer system.

10. The swing training device, as in claim 1, wherein the swing training device is further comprised of:
a magnetized, adjustable retaining rod removably attached to the removable magnetized end cap at one end of the magnetized retaining rod such that the adjustable weight is retained on the other end of the magnetized retaining rod.

11. The swing training device, as in claim 1, wherein the adjustable weight is further comprised of:
a durable, rigid, high impact resistant, crack resistant, temperature resistant, wear resistant, UV stabilized metallic material.

12. The swing training device, as in claim 11, wherein the adjustable weight is further comprised of:
a spherical ball.

13. A one-piece swing training device for use on sporting implements having a substantially straight shaft, comprising:
a tapered sporting implement attachment section having a narrower end portion located at one end of the sporting implement attachment section and a wider end portion located at another end of the sporting implement attachment section;
a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained on the removable magnetized end cap; and
an adjustable insert located within the sporting implement attachment section such that the adjustable insert interacts with a section of a sporting implement having a substantially straight shaft to assist in retaining the swing training device on the sporting implement.

14. The swing training device, as in claim 13, wherein the adjustable insert is further comprised of:
a sporting implement sleeve having sleeve end portions.

15. The swing training device, as in claim 14, wherein the removable end cap is constructed of a durable, rigid, scratch resistant, haze resistant, high impact resistant, crack resistant, temperature resistant, wear resistant, UV stabilized material, wherein the material is selected based upon the type of sound that is needed in order to provide an audible feedback to the user.

16. The swing training device, as in claim 13, wherein the sporting implement attachment section is further comprised of:
an accelerometer system.

17. The swing training device, as in claim 13, wherein the swing training device is further comprised of:
a magnetized, adjustable retaining rod removably attached to the removable magnetized end cap at one end of the magnetized retaining rod such that the adjustable weight is retained on the other end of the magnetized retaining rod.

18. A method of using a swing training device, wherein the swing training device includes a tapered sporting implement attachment section and a cylindrical section operatively attached to the sporting implement attachment section wherein the cylindrical section includes a cylindrical tube, a weight retainer located at one end of the cylindrical tube and a removable end cap located at another end of the cylindrical tube, wherein the weight retainer includes a removable magnetized end cap and an adjustable weight magnetically retained to the removable magnetized end cap, comprising the steps of:
selecting, by a user, a type of a sporting implement to be used by the user,
selecting a size of a swing training device that is to be removably attached to the sporting implement;
selecting a desired magnetic strength of a removable, adjustable magnetized end cap;
selecting a desired size of an adjustable weight;
inserting the weight into a cylindrical tube;
fastening the removable magnetized end cap to the cylindrical tube;
attaching the weight to the magnetized end cap;
attaching the sporting implement attachment section to the sporting implement positioning the user in an initial swing stance;
swinging the sporting implement such that wrists of the user are rolled thereby causing the adjustable weight to become separated from the magnetized end cap;
impacting the removable end cap with the adjustable weight thereby causing the removable end cap to emit a sound and a light which are determinative as to when wrists of the user were rolled; and
measuring a velocity at which the user is swinging the sorting implement.

* * * * *